United States Patent [19]
Friend et al.

[11] Patent Number: 6,139,865
[45] Date of Patent: Oct. 31, 2000

[54] TASTE-MASKED MICROCAPSULE COMPOSITIONS AND METHODS OF MANUFACTURE

[75] Inventors: David R. Friend, Menlo Park; Steve Ng, San Francisco, both of Calif.; Rafael E. Sarabia, Chester, N.J.; Thomas P. Weber, Shoreview, Minn.; Jean-Marie Geoffroy, Grayslake, Ill.

[73] Assignee: Eurand America, Inc., Vandalia, Ohio

[21] Appl. No.: 08/942,094

[22] Filed: Oct. 1, 1997

Related U.S. Application Data

[60] Provisional application No. 60/027,170, Oct. 1, 1996.

[51] Int. Cl.⁷ .............................. A61K 9/20; A61K 9/50; A61K 9/58; A61K 9/62
[52] U.S. Cl. .................... 424/441; 424/465; 424/466; 424/490; 424/494; 424/495; 424/497; 514/937; 514/963; 514/974
[58] Field of Search ................................. 424/441, 464, 424/466, 490, 465, 494, 495, 497

[56] References Cited

U.S. PATENT DOCUMENTS

| | | | |
|---|---|---|---|
| 3,860,733 | 1/1975 | Morse et al. | 426/302 |
| 4,389,330 | 6/1983 | Tice et al. | 427/213.36 |
| 4,389,331 | 6/1983 | Samejima et al. | 427/213.36 |
| 4,542,042 | 9/1985 | Samejima et al. | 427/213.36 |
| 5,075,114 | 12/1991 | Roche | 424/470 |
| 5,082,669 | 1/1992 | Shirai et al. | 424/495 |
| 5,084,278 | 1/1992 | Mehta | 424/441 |
| 5,622,723 | 4/1997 | Bettman et al. | 424/495 |

FOREIGN PATENT DOCUMENTS

93/24109 12/1993 WIPO.

OTHER PUBLICATIONS

"Taste Masking in Oral Pharmaceuticals", *Pharmaceutical Technology*, Apr. 1994 p. 84–99.

"Some Properties of Chloroquine phosphate and Quinine Hydrochloride Microcapsules", *S.T.P. Pharma. Sciences* 1(2):117–120 (1991), A. Chukwu et al.

Recent Pharmaceutical Techniques and Outlook for masking the Bitter Taste of Granules, *Gifu Yakuke Daigaku Kŝyo* 44:18–31 (1995).

*Primary Examiner*—James M. Spear
*Attorney, Agent, or Firm*—Thompson Hine & Flory LLP

[57] ABSTRACT

A taste-masked microcapsule composition for administration of a drug is provided. The composition comprises microcapsules of drug and a substantially water-insoluble polymeric material, typically a cellulosic polymer. The microcapsule composition may be incorporated into any number of pharmaceutical formulations, including chewable tablets, effervescent tablets, powders, liquid dispersions, and the like. A method for masking the taste of drugs is also provided, involving a phase separation coacervation technique in which drug is coated with relatively high levels of a polymeric material. These high coating levels give rise to effective taste masking, while nevertheless allowing targeted release of drug, so that the drug is released shortly after passage through the mouth.

47 Claims, 4 Drawing Sheets

TASTE-MASKED MICROCAPSULE COMPOSITIONS AND METHODS OF MANUFACTURE

CROSS REFERENCE TO RELATED APPLICATIONS

The present application claims benefit of U.S. Provisional Application Ser. No. 60/027,170, filed Oct. 1, 1996, the disclosure of which is hereby incorporated by reference herein.

FIELD OF THE INVENTION

This invention relates generally to pharmaceutical compositions in the form of microcapsules, and more particularly relates to such microcapsules in which the taste of the drug contained therein is tastemasked. The invention additionally relates to pharmaceutical formulations containing the microcapsules, including effervescent formulations, and to a process for masking the taste of drugs using a phase separation-coacervation technique.

BACKGROUND OF THE INVENTION

A number of methods are known for masking the taste of drugs; this is an increasingly important issue in the area of patient compliance with recommended pharmaceutical therapies. As explained by M. Ueda in "Recent Pharmaceutical Techniques and Outlook for Masking the Bitter Taste of Granules," *Gifu Yakuke Daigaku Kfyo* 44:18–31 (1995), taste masking techniques may be broadly divided into physical, chemical, biochemical and organoleptic methods. The technique to be adopted will depend on several factors, but primarily on the extent of bitterness of the drug to be incorporated into an oral pharmaceutical formulation.

Organoleptic methods of taste-masking involve addition of a flavoring and/or sweetening agent and as such are relatively simple. However, simple addition of a taste-masking agent such as a flavoring agent or sweetener is frequently not useful by itself, unless the drug to be taste-masked is not particularly bitter. Recent biochemical methods involve the use of lipoproteins to react with bitterness receptor sites, thereby suppressing the response to the drug's bitterness. The most common masking methods, however, are based on physical means, including agglomeration, coating, and microencapsulation. Microencapsulation is essentially a process by which coatings are applied to small particles of solids, droplets of liquids or dispersions, so as to form microcapsules; the technique differs from other coating procedures in that the size of the particles generally ranges from several tenths of a $\mu$m to 5000 $\mu$m in diameter.

The present invention involves the use of a microencapsulation technique to taste mask drugs in an oral pharmaceutical formulation. The microencapsulation technique is a coacervation-phase separation process which involves utilization of three phases: a "core material" phase of the drug to be encapsulated; a "coating material" phase of the substance which will ultimately form the coating; and a liquid phase in which the core and coating materials are dispersed or dissolved. The coating is then deposited on the core material, and a desolvation process is used to remove the liquid phase and isolate the microcapsules. In contrast to prior microencapsulation techniques, the present invention makes use of materials and process parameters which enable preparation of uniform, impervious coatings, and involves preparation of formulations having high coating levels. In this way, the invention provides for extremely effective taste masking while also providing for release of drug shortly after the drug passes through the mouth. Generally, as will be appreciated by those working in the field, it is very unusual and quite difficult to achieve fast drug release with high coating levels effective in taste masking. The invention, having achieved these objectives, thus provides for an important advance in the art, enabling effective taste masking of a variety of drugs.

OVERVIEW OF THE ART

Roy, "Taste Masking in Oral Pharmaceuticals," *Pharmaceutical Technology*, April 1994, at pages 84–99, is a review article which addresses a number of methods and formulations for masking or improving the taste of normally bitter drugs. Coating ranitidine hydrochloride with ethyl cellulose is mentioned as a possible way to achieve taste masking of the drug.

U.S. Pat. No. 5,075,114 to Roche describes a fluidized bed method of coating a pharmaceutical agent for taste-masking purposes. The patent describes the coating as a blend of cellulosic materials, i.e., hydroxypropyl cellulose and either cellulose acetate, cellulose acetate butyrate, or both. A number of drugs are mentioned, including ibuprofen, loperamide, famotidine, cimetidine, and ranitidine.

U.S. Pat. No. 5,082,669 to Shirai et al. describes ethyl cellulose coatings for bitter-tasting drugs. A number of drugs are mentioned as possibilities (at column 3, lines 13–31), including cimetidine. The coating is prepared using either a film-forming solution or dispersion, or a spraying technique (column 5, lines 36–50).

A. Chukwu et al., "Some Properties of Chloroquine Phosphate and Quinine Hydrochloride Microcapsules," *S.T.P. Pharma. Sciences* 1(2):117–120 (1991) describes methods for microencapsulating chloroquine phosphate and quinine hydrochloride particles with ethyl cellulose using a thermally induced coacervation technique and cyclohexane as a solvent.

U.S. Pat. No. 4,389,330 to Tice et al. describes a method for making microencapsulated drugs using a "wall forming material" which may be cellulosic (column 3, line 22) in conjunction with a solvent such as methylene chloride. The method is stated to be useful in connection with a wide variety of drugs, including gastrointestinal therapeutic agents.

U.S. Pat. Nos. 4,389,331 and 4,542,042 to Samejima et al. describe a method for encapsulating drugs with ethyl cellulose using a phase separation technique. In the '331 patent, phospholipids are used to induce phase separation; in the '042 patent, another type of compound is used, i.e., a hydrocarbon such as a wax, butyl rubber, or polyethylene is used.

One process which purportedly provides taste-masked microcapsules of certain bitter-tasting drugs such as $H_2$ antagonists, and which also purportedly provides rapid release of the drugs from the microcapsules, is set forth in PCT Published International Application WO 93/24109. This process, however, utilizes multiple coating layers applied by an air suspension coating technique, rather than by coacervation. The coatings consist of cellulosic polymers having quaternary ammonium groups to enhance permeability of the drug through the polymers. Application of large amounts of a coating through a spray-coating technique or an air suspension technique, is a time-consuming process.

Although the use of polymeric materials, particularly cellulosic polymers, to taste mask bittertasting drugs is known, as noted above, the present invention provides for far more effective taste masking than previously possible, using high coating levels while nevertheless achieving virtually immediate release of drug.

SUMMARY OF THE INVENTION

Accordingly, it is a primary object of the invention to address the above-mentioned need in the art by providing taste-masked microcapsules for oral administration of a drug, preferably a water-soluble drug, wherein the microcapsules have high coating levels but are nevertheless effective to achieve rapid release of drug.

It is another object of the invention to provide H2 antagonists such as ranitidine or a pharmaceutically acceptable acid addition salt thereof, in taste-masked form.

It is still another object of the invention to provide a method for manufacturing an oral pharmaceutical formulation comprising microcapsules in which the drug contained therein is taste masked.

It is yet another object of the invention to provide a method for manufacturing such an oral pharmaceutical formulation using a phase separation-coacervation technique in which the coating material represents on the order of 30 wt. % to 65 wt. % of the final, dried microcapsule formulation.

Additional objects, advantages and novel features of the invention will be set forth in part in the description which follows, and in part will become apparent to those skilled in the art upon examination of the following, or may be learned by practice of the invention.

DETAILED DESCRIPTION OF THE PREFERRED EMBODIMENTS

Figure 1A:
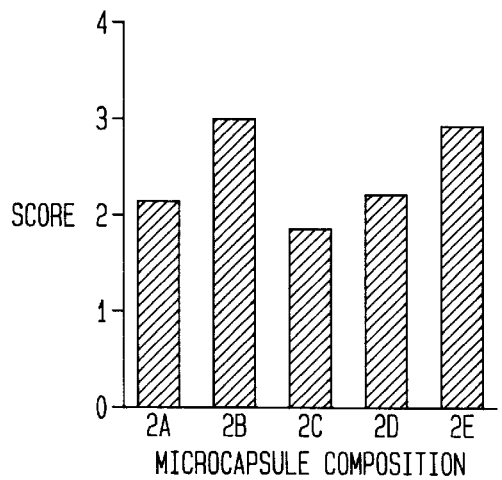
FIG. 1A, FIG. 1B, FIG. 1C, and FIG. 1D depict the average scores for the evaluation described in Example 6 of taste masking, bitterness, aftertaste, and overall acceptance, respectively, of ranitidine microcapsule compositions.

Before describing the present invention in detail, it is to be understood that this invention is not limited to particular pharmaceutical formulations, process parameters, or coating materials as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a polymeric material" includes a mixture of two or more polymeric materials, reference to "a solvent" includes reference to two or more solvents, reference to "an excipient" or "a vehicle" includes mixtures of excipients or vehicles, reference to "a drug" includes reference to two or more drugs, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

The term "drug" as used herein is meant to include any therapeutic or otherwise active agents, preferably a pharmaceutical compound or chemical that is capable of being orally administered. Drugs useful in conjunction with the present invention include antibiotics, antiviral agents, analgesics, anesthetics, anorexics, antiarthritics, antiasthmatic agents, anticonvulsants, antidepressants, antidiabetic agents, antidiarrheals, antihistamines, anti-inflammatory agents, antinauseants, antineoplastics, antiparkinsonism drugs, antipruritics, antipsychotics, antipyretics, antispasmodics, $H_2$ antagonists, cardiovascular drugs, antiarrhythmics, antihypertensives, ACE inhibitors, diuretics, vasodilators, hormones, hypnotics, immunosuppressives, muscle relaxants, parasympatholytics, parasympathomimetics, psychostimulants, sedatives, antimigrane agents antituberculosis agents and tranquilizers. Generally, the drugs used in conjunction with the present methodology are those which are bitter or otherwise unpleasant-tasting and thus in need of taste masking. Specific such drugs include ranitidine, cimetidine, famotidine, guaifenesin, loperamide hydrochloride, nizetidine, dimenhydrinate, caffeine, theophylline, acetaminophen and ibuprofen. The term "drug" is also intended to include nutritional supplements, particularly those in the vitamin B family and vitamin C.

By an "effective" amount of drug is meant a nontoxic but sufficient amount of a compound to provide the desired therapeutic or prophylactic effect.

The term "polymer" as used herein is intended to include both oligomeric and polymeric materials, i.e., compounds which include two or more monomeric units. The term is also intended to include "copolymeric" materials, i.e., containing two or more different monomeric units.

"Carriers" or "vehicles" as used herein refer to carrier materials suitable for oral drug administration, and include any such materials known in the art, e.g., diluents, binders, granulating agents, disintegrants, lubricating agents, colorants, flavoring agents, and the like. The term "microencapsulation" is used to refer to a process for forming coated drug particles. The "microcapsules" so formed may be in the nature of a drug core having a polymeric coating thereon; alternatively, the capsules may comprise polymer matrices containing infiltrated drug.

The term "pharmaceutical formulation" as used herein refers to formulations containing the microcapsules of the invention in combination with carriers or excipients suited to a selected drug delivery platform, e.g., an effervescent formulation, a chewable tablet, a fast-melting formulation, or the like. "Microencapsulation conducted by phase separation" and "coacervation" intends an encapsulation process in which drug is dispersed in a solution containing a coating material, and procedures are then followed which result in deposition of the coating on the core material.

More specifically, the microcapsules of the invention are prepared by first admixing the selected drug, a first polymeric material to serve as the coating, and a second polymeric material to promote phase separation, in a nonpolar organic solvent. Mixing is preferably conducted along with stirring or agitation using any number of conventional means. The solvent should be one in which the polymeric materials are soluble at higher temperatures, i.e., temperatures generally on the order of 70° C. or higher, but insoluble at ambient temperature; also, the drug should be substantially insoluble in the solvent at all temperatures used in the manufacturing process. A particularly preferred solvent for the present purpose is cyclohexane; however, it will be appreciated by those skilled in the art that other nonpolar organic solvents are also effective and could be used as well.

It is important to choose the relative quantities of drug and first polymeric material carefully; generally, the relative quantities are such that the microcapsules contain approximately 30 wt. % to 65 wt. % first polymeric material, preferably 40 wt. % to 60 wt. % first polymeric material, and most preferably 45 wt. % to 55 wt. % first polymeric material. At these high coating levels, effective taste masking of drug is achieved.

After admixture of these initial components, the suspension so formed is heated for a time period and to a temperature sufficient to dissolve the first and second polymeric materials in the solvent. In addition, stirring is preferably continued at a predetermined stirring rate; a suitable stirring rate may be readily determined by one skilled in the art. The temperature is at or below the boiling point of the solvent; generally the components will be heated to a temperature of 70° or higher, and preferably to a temperature of at least about 75° C. However, care must be taken not to heat to a temperature which could degrade the drug (for ranitidine hydrochloride, temperatures higher than about 85° C. should be avoided). Cooling is then effected at a rate and to a temperature sufficient to effect phase separation of the first polymeric material and microencapsulation of the drug therein, forming a dispersion of microencapsulated drug. It will be appreciated by those skilled in the art that the cooling rate can be varied to optimize properties of the microcapsules, e.g., with respect to aggregation, flowability and release profile. The solvent and second polymeric material are then removed by decanting, filtering or the like, followed by washing with solvent to remove any traces of the second polymeric material, and then drying, again at a temperature not so high that the drug or coating material could be adversely affected. Drying is usually although not necessarily conducted for at least about 6 hours, and longer for large-scale batches, at a temperature generally in the range of approximately ambient temperature to 60° C. Drying may or may not be conducted under reduced pressure.

A variation on the aforementioned procedure provides a valuable alternative method which may be preferred for heat-sensitive drugs. This alternative procedure involves dissolving the first and second polymeric materials in the selected nonpolar organic solvent, without addition of drug, followed by heating to a temperature effective to dissolve the polymers. Drug is then added, the mixture is then allowed to cool, and the remainder of the procedure described above is carried out.

The selected drug, as noted hereinabove, is typically a bitter or otherwise unpleasant treating drug such as ranitidine, cimetidine, or the like. The drug may also be in the form of a pharmaceutically acceptable salt, typically an acid addition salt such as may be formed by treating the base form of the drug with a stoichiometric excess of a selected acid. Such acid addition salts may be prepared, for example, with inorganic acids such as hydrochloric acid, hydrobromic acid, sulfuric acid, nitric acid, phosphoric acid, and the like, or with organic acids such as acetic acid, propionic acid, glycolic acid, pyruvic acid, malic acid, malonic acid, succinic acid, maleic acid, hydroxymaleic acid, fumaric acid, tartaric acid, citric acid, benzoic acid, cinnamic acid, mandelic acid, p-toluenesulfonic acid, naphthalene-2-sulfonic acid, salicylic acid and the like. With acidic drugs, by analogy, pharmaceutically acceptable salts may be prepared with bases such as potassium hydroxide, ammonium hydroxide, magnesium hydroxide, sodium hydroxide, calcium hydroxide, with naturally occurring amines such as trimethylamine, diethylamine, ethanolamine, with basic ion exchange resins, or the like.

While any number of drugs can be used in conjunction with the present process and formulations, certain preferred drugs are water-soluble, i.e. drugs which are soluble or very soluble in water according to the definitions of the terms "soluble" or "very soluble" as defined in the United States Pharmacopeia, XXIII edition. According to such definition, one gram of a soluble drug can be dissolved in 30 ml of water, and preferably in 10 ml of water, at 20–25° C., whereas one gram of a very soluble drug can be dissolve in 1 ml of water, also at 20–25° C. Thus, the preferred water soluble drugs used in the present invention are those having solubility of one gram of drug in 30 ml, more preferably in 10 ml and most preferably in 1 ml of water at 20–25° C. Desirably, the drugs have relatively low molecular weight, below 5000, preferably below 1000 and preferably below 500.

The present invention is particularly useful with those drugs having an unpleasant taste. Thus, although the invention can be used to mask the taste of drugs which have a pleasant taste, and can also be used to administer drugs which have no appreciable taste, the greatest benefit is achieved with those drugs having unpleasant tastes such as bitter taste. As disclosed, for example in Handbook of Sensory Physiology, Volume IV, Chapter, bitter tasting compounds typically incorporate certain characteristic structures. These include N-containing ring structures such as purine, pyridiene and pyrrole rings, commonly found in alkaloids; multiple $NO_2$ groups; $C=S$ and $—S—S—$ moieties; and urea-like structures, i.e.,

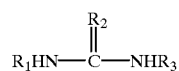

Where R1, R2 and R3 may be the same or different. Other bitter tasting compounds include certain salts and glycosides. The $H_2$-antagonists discussed below are bitter-tasting compounds.

Another preferred class of drugs are water-soluble $H_2$-antagonists, more preferably $H_2$-antagonists selected from the group consisting of ranitidine; famotidine; cimetidine; nizatidine. Pharmaceutically acceptable water-soluble salts of such $H_2$-antagonists and combinations of such $H_2$-antagonists and/or salts may also be employed. Pharmaceutical compositions prepared with the $H_2$antagonist ranitidine, and particularly ranitidine hydrochloride, are particularly preferred herein. Ranitidine, or N-[2[[[5-[dimethylamino)methyl]-2-furanyl]-methyl⁻thio]ethyl]-N'-methyl-2-nitro-1,1-ethenediamine, is described in U.S. Pat. No. 4,128,658 to Price et al., assigned to Glaxo. Reference may be had thereto for any information concerning methods for synthesizing or using ranitidine not explicitly included herein.

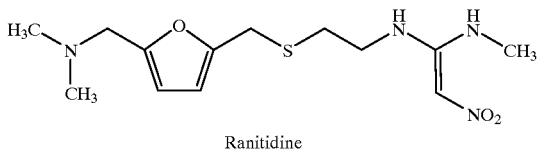

Ranitidine

As explained in the '658 patent, ranitidine and other aminoalkyl furan derivatives have been identified as inhibitors of the secretion of gastric acid when stimulated via histamine $H_2$-receptors. The '658 patent also indicates that ranitidine and analogs thereof are useful in the treatment of conditions where there is a hypersecretion of gastric acid, e.g., in gastric and peptic ulceration, in the treatment of allergic conditions where histamine is a known mediator, and in the treatment of allergic and inflammatory conditions such as urticaria.

Turning now to the remaining formulation components, the first polymeric material is one that (1) is effective to microencapsulate the drug upon completion of the process, (2) is "substantially water-insoluble," and has appreciable solubility in the selected nonpolar organic solvent i.e.-, the solubility in the selected nonpolar organic solvent is such that the phase separation-coacervation process can be carried out in that solvent, (3) provides for effective taste masking of the drug; and (4) prevents immediate release of the microencapsulated drug in the mouth. Ethyl cellulose is particularly preferred as the first polymeric material, although other polymers can be used as well, e.g., cellulose acetate phthalate, cellulose acetate butyrate, polymethacrylates, hydroxypropyl methyl cellulose phthalate; carboxymethyl ethylcellulose; and polylactic acid and the like. The most preferred polymers for use as the first polymeric material are the specifically named polymers, in the preceding sentence and combinations of such polymers. The preferred polymers are substantially free of readily ionizable substituents such as quaternary ammonium groups and preferably are essentially or entirely free of such substituents. Although derivatives of the preferred polymers with substituents such as non-polar substituents can be employed, the most preferred forms of such polymers are essentially free of all substituents. Unless otherwise indicated herein, references to specific named polymers used as the first polymeric material are intended to refer to the polymers as named, essentially free of substituents. Certain preferred polymers have very low solubility for the drug incorporated in the microcapsules, and hence a very low rate of diffusion of the drug through the bulk of the polymer. As further discussed below, it is believed that release of the drug from the microcapsules principally involves pores in the coating rather than diffusion of the drug through the first polymeric material itself.

The second polymeric material is selected such that it is ffective in assisting phase separation of the first polymeric material in the aforementioned process. Although polyethylene is preferred, other polymers may be used as well, e.g., polyisobutylene, ethylenevinyl acetate, and the like. Still other polymers which may serve to promote phase separation may also be used, and such polymers will be known to or may be readily deduced by those skilled in the art. The amount of second polymeric material should be selected so as to be at least minimally sufficient to promote phase separation.

In a variation on this basic process, the second polymer may be omitted, so long as alternative means are provided for promoting phase separation of the first polymeric material and formation of microcapsules. Typically, this process will involve addition of a second solvent effective to assist in and/or induce phase separation of the first polymeric material and microencapsulation of the drug.

Optional additives which may be incorporated into the microcapsules include deagglomeration agents, i.e., agents effective to reduce microcapsule aggregation (e.g., colloidal silica such as that available as Syloid®), colorants (e.g., titanium dioxide, dyes suitable for food such as those known as F.D. & C. dyes, etc.), flavoring and/or sweetening agents, and the like. However, additives which materially affect the release of the drug preferably are not present in the first polymer layer of the microcapsule. That is, the polymeric portion of the microcapsule desirably consists essentially of the first polymer, with or without residual amounts of the second polymer. Trace amounts of the non-polar solvent used in the process may also remain, provided the solvent has an acceptably low toxicity at the levels remaining in the microcapsules. Preferably, the microcapsules are not coated with any additional layer surrounding the polymeric portion of the capsule. If any such additional layer is employed, it should be formed from a material which is highly water-soluble or should include at least about 10%, and desirably at least about 15%, of a material which is highly water soluble, so that all or part of the coating will be removed promptly when the microcapsule comes in contact with saliva and/or gastric fluid during use.

Generally, although not necessarily, the particle size of the microcapsules will be in the range of a few microns up to about a thousand microns or more, with particle sizes in the approximately 30 µm to 800 µm preferred, and particle sizes in the range of approximately 40 µm to 250 µm particularly preferred.

Those skilled in this art will recognize that the components of the microcapsules, the relative quantities of drug and polymeric coating material, the size of the microcapsules, and other parameters, can easily be varied to provide for different degrees of taste masking and various release profiles. The process parameters, microcapsule components, and relative quantities of components described hereinabove will generally provide a "targeted" release profile, i.e., wherein drug release does not generally occur in the mouth, but does occur very shortly thereafter, and is virtually complete within a matter of minutes. In quantitative terms, the targeted-release microcapsules desirably provide dissolution of at least about 75% of the drug within 45 minutes when tested according to the United States Pharmacopeia, ("USP") dissolution test, using Apparatus 2, commonly referred to in the art as the "paddle method" dissolution test. The dissolution test referred to herein should be conducted using the dissolution medium, stirring speed and amount of dissolution medium specified in the USP monograph for tablets or capsules of the active ingredient contained in the microcapsules. If no such USP monograph exists, or if the aforementioned conditions are not specified, 900 ml of water should be used as the dissolution medium for microcapsules containing less than 5 % of the amount required to form a saturated solution of the active ingredient in 900 ml of water. The stirring speed should be 50 rpm, and the temperature should be 37° C. Still higher values of dissolution at 45 minutes, such as at least about 90% dissolution at 45 minutes, are even more desirable. Also, the ability to provide at least about 75% or even greater dissolution at dissolution times of about 30 minutes, or even more preferably at dissolution times of about 15 minutes, is even more preferred. Where the USP monograph for immediate-release tablets or capsules of the active ingredient states a quantity as a percentage Q of the active ingredient to be dissolved in a dissolution test, the microcapsules according to preferred embodiments of the present invention desirably provide dissolution of at least that quantity, and preferably Q+5 percent, in the same dissolution test as specified in the monograph. Stated another way, the targeted release microcapsules according to the present invention should have a dissolution rate at least as rapid as required to provide the dissolution properties specified in the USP monograph for immediate release tablets or capsules of the active ingredient.

However, the targeted release should not be instantaneous in saliva, as instantaneous release of the drug in the patient's mouth would impair taste masking. Thus, substantial dissolution of the drug during dissolution times of about 1 minute or less, is generally not desirable. When the microcapsules are used in a pharmaceutical dosage form, they are typically swallowed and pass through the mouth in about 1 minute or less. Lower levels of dissolution during the first minute are associated with more effective taste masking. An ideal taste-masking microcapsule would allow no dissolution of the drug at all in one minute. Thus, the preferred microcapsules should allow dissolution of considerably less than 75% of the drug in one minute according to the aforementioned USP test method; lower values of dissolution at one minute such as less than 50%, less than 25% less than 5% and less than 1% are still more preferred.

Although the present invention is not limited by any theory of operation, it is believed that the polymeric walls of the microcapsules, particularly those formed by coacervation, typically have pores. It is further believed that drug dissolution from the microcapsules occurs through these pores. Thus, it is believed that water enters the pores and forms a highly concentrated solution of drug and water inside the microcapsule, and that the resulting concentration gradient from the highly concentrated solution to the surrounding aqueous fluid drives diffusion of the drug out through the pores to the surrounding aqueous fluid. Another mechanism of release which is believed to occur is breakage of the coating on the microcapsule, possibly caused or promoted by swelling of the core material due absorption of water. Regardless of the theory of operation, higher proportions of coating material in the microcapsules tend to provide slower dissolution, whereas coacervation processes using lesser amounts of the coacervation promoting agent or "second polymer" referred to above tend to provide more rapid dissolution. The latter effect is believed to arise from the influence of the second polymer on pore formation; greater amounts of the second polymer tend to promote formation of polymer coatings with fewer or smaller pores. Regardless of the reasons for these effects, these effects can be used to adjust the release rate for a particular drug.

Various types of pharmaceutical formulations may be prepared using the presently disclosed microcapsules, including powders, chewable tablets, rapidly dissolving tablets, effervescent formulations, and liquid dispersions. For solid formulations such as powders, chewable tablets and effervescent formulations, conventional carriers, excipients and additives will be employed, including diluents, binders, granulating agents, disintegrants, flavoring additives, and the like. Examples of the normally employed excipients include pharmaceutical grades of mannitol, lactose, starch, and the like. Liquid pharmaceutical compositions containing the present microcapsules will generally be prepared by dispersing or suspending the microcapsules in a non-aqueous carrier which does not cause release of the drug, or else by dispersing the microcapsules in an aqueous carrier immediately prior to administration to the patient. For example, the microcapsules may be provided as a free-flowing particulate material, as in a sachet or other suitable package, and such a particulate material may be dispersed in an aqueous carrier. These solid or liquid formulations may contain any amount of the microcapsules needed to provide the desired amount of the active ingredient contained in the microcapsules. For example, amounts of microcapsules on the order of 10 wt. % to 95 wt. % of the dosage form may be used. The dosage form should be configured to provide rapid release of the microcapsules when administered to the patient. Stated another way, the elements of the dosage form other than the microcapsules should not greatly impede release of the active ingredient within the microcapsules when the dosage form is administered to a patient. Thus, the dosage form desirably provides dissolution values such as the preferred dissolution values discussed above with respect to the microcapsules. Actual methods of preparing such dosage forms are known, or will be apparent, to those skilled in this art; for example, see *Remington's Pharmaceutical Sciences*, 18th Edition (Easton, Pennsylvania: Mack Publishing Company, 1990).

With regard to effervescent formulations, the procedures and components employed will generally although not necessarily be those described in U.S. Pat. Nos. 5,178,878, 5,219,574, 5,223,264 and 5,401,513, all to Wehling et al. and of common assignment herewith, and each of which is incorporated by reference in its entirety. The formulations incorporate components to promote effervescence, i.e., release of gas upon contact with water; these components include a dry, solid carbonate salt, preferably sodium bicarbonate, and an organic acid such as citric, tartaric, malic, fumaric, adipic and succinic acids. These additives in combination typically represent on the order of 1 wt. % to 90 wt. %, preferably 2 wt. % to 50 wt. %, and most preferably 2 wt. % to 25 wt. % of the effervescent tablet, and liberate carbon dioxide upon contact with water. The effervescent formulations may additionally include pharmaceutical grade lubricants such as hydrogenated and partially hydrogenated vegetable oils, animal fats, polyethylene glycol, polyoxyethylene monostearate, talc, light mineral oils, sodium benzoate, sodium lauryl sulfate, magnesium oxide, magnesium stearate, stearic acid, glyceryl behenate, the lubricant sold under the trademark MYVATEX TL by Eastman Chemicals, and the like. As described for example in the aforementioned U.S. Pat. No. 5,118,878, effervescent tablets suitable for direct oral administration are particularly useful. Such tablets can be arranged to disintegrate rapidly under upon exposure to saliva when placed in the mouth, thereby reducing or eliminating the need for chewing by the patient to cause disintegration. As explained in the '878 patent, this tends to minimize damage to microcapsules incorporated in such an effervescent dosage form.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g, amounts, temperature, etc.) but some experimental error and deviation should be accounted for. Unless indicated otherwise, temperature is in degrees C and pressure is at or near atmospheric.

EXAMPLE 1

Preparation of Encapsulated Ranitidine

The following process was used to prepare ranitidine microcapsules.

Ethyl cellulose (120 g; NF Premium Standard Grade, 100; Dow Chemical) and 249.2 g ethylene vinyl acetate copolymer (Elvax® 40; DuPont) were added to eight liters of cyclohexane in a twelve-liter flask. The mixture was heated to 80° C. until all of the polymer was dissolved. Ranitidine hydrochloride (80 g; Glaxo) was added to the polymer solution and the mixture was stirred at 450 rpm for 1 hr. The resultant solution was allowed to cool with stirring at 450 rpm at about 0.5° C./min for 1 hr to a final temperature of about 50° C. The solution was then cooled to 40° C. at 0.166° C./min over a period of one hour. Finally, the solution was cooled to 20° C. by immersing the flask in ice water. The resultant solid precipitate was allowed to settle and the cold solution was decanted. The solid was collected by filtration and washed twice with one liter of cold cyclohexane and once with one liter of cyclohexane. The resultant mass of microcapsules was allowed to air dry overnight and then dried under reduced pressure for at least six hours. The dried microcapsules (about 195 g) were dispersed gently, if necessary, with a mortar and pestle and then sieved through an 840 μm screen. Approximately 5% of the product was retained by the screen. This overall process yielded 185 g of product.

EXAMPLE 2

Preparation of Encapsulated Ranitidine. Reproducibility

Five batches of microcapsules containing granular ranitidine hydrochloride were prepared by the method described in Example 1. Polyethylene was substituted for the ethylene vinyl acetate copolymer. The formulations for these microcapsules is given in Table 1 and, as may be 10 seen in the table, each contain 5 wt. % colloidal silica (Syloid(®) as a deagglomerating agent. Batches 1, 4 and 5 (experiments 2A, 2D and 2E) were identical formulations.

TABLE 1

| Experiment # | 2A | 2B | 2C | 2D | 2E |
| --- | --- | --- | --- | --- | --- |
| Batch Size | 5 gallon | 5 gallon | 5 gallon | 5 gallon | 5 gallon |
| Ethylcellulose Conc.[15] STD 100 cps (In Final Product) | 5% (45%) | 5% (55%) | 5% (35%) | 5% (45%) | 5% (45%) |
| Ranitidine HCl Conc.[16] (Mean Particle Size) [Supplier] | 55% granular [Glaxo] | 45% granular [Glaxo] | 65% granular [Glaxo] | 55% granular [Glaxo] | 55% granular [Glaxo] |
| Polyethylene Conc.[17] | 0.5% | 0.5% | 0.5% | 0.5% | 0.5% |
| Agitation RPM | 300 rpm | 300 rpm | 300 rpm | 300 rpm | 300 rpm |
| Syloid ® Conc.[18] | 5% | 5% | 5% | 5% | 5% |
| Drying Method | @ 50° C. | @ 50° C. | @ 50° C. | @ 50° C. | @ 50° C. |
| Drying Time | 14–15 hours | 14–15 hours | 14–15 hours | 14–15 hours | 14–15 hours |
| Cyclohexane Content on Finished Microcaps | NMT 300 ppm | NMT 300 ppm | NMT 300 ppm | NMT 300 ppm | NMT 300 ppm |
| Polyethylene Content on Finished Microcaps | NMT 0.1% | NMT 0.1% | NMT 0.1% | NMT 0.1% | NMT 0.1% |

[15]Concentration of ethycellulose is based on 5% of total cyclohexane weight/volume.
[16]Concentration of ranitidine HCl is based on ratio to ethylcellulose in the final microcapsules.
[17]Concentration of polyethylene is based on 0.5% of total cyclohexane weight.
[18]Concentration of Syloid ® is based on 5% of total solids (ethylcellulose and ranitidine HCl).

EXAMPLE 3

Microcapsule Evaluation

The purpose of this Example 3 was to evaluate the release profile of the microcapsules prepared in Example 2. In Table 2, drug release was evaluated as a function of time for each batch of microcapsules. As may be seen, virtually all of the microcapsules released the majority of encapsulated drug therein within a five minute time period, with over 90% of drug released in 30 to 45 minutes for all microcapsules evaluated.

| Experiment # | 3A | 3B | 3C | 3D | 3E |
| --- | --- | --- | --- | --- | --- |
| Material Received | 600 gm | 500 gm | 900 gm | 600 gm | 600 gm |
| Theroretical Ethylcellulose Coating Level | 45% | 55% | 35% | 45% | 45% |
| Ranitidine Base Potency[19] (Mean Particle Size) [Supplier] | 46.33% granular [Glaxo] | 35.04% granular [Glaxo] | 56.18% granular [Glaxo] | 46.24% granular [Glaxo] | 47.31% granular [Glaxo] |
| Cyclohexane Content in | 71 ppm | 160 ppm | 13 ppm | 87 ppm | 71 ppm |

-continued

| Experiment # | 3A | 3B | 3C | 3D | 3E |
|---|---|---|---|---|---|
| Finished Microcaps Polyethylene Content in Finished Microcaps | 0.25% | 0.38% | 0.25% | 0.31% | 0.33% |
| Drug Release | | | | | |
| 5 min | 66.5% | 63.2% | 76.8% | 70.6% | 71.1% |
| 15 min | 85.5% | 80.5% | 89.2% | 87.6% | 88.9% |
| 20 min | 89.3% | 84.2% | 91.2% | 90.8% | 92.0% |
| 30 min | 93.3% | 88.8% | 92.7% | 94.0% | 95.1% |
| 45 min | 96.1% | 92.3% | 93.6% | 96.0% | 96.9% |
| 60 min | 97.4% | 94.2% | 94.2% | 97.0% | 97.8% |

EXAMPLE 4

Formulation of Effervescent Tablets Containing Ranitidine HCl Microcapsules

Microcapsules containing ranitidine hydrochloride were prepared as described in Example 2. Effervescent tablets containing such microcapsules were prepared by weighing the components listed in Table 3 into a poly bag. The admixture thus prepared was passed through a 16US-mesh screen, added to a twin-shell blender and blended for 15 minutes. The lubricant, magnesium stearate, was screened, weighed, and added to the mixture in the twin-shell blender. Blending was continued for an additional 5 minutes. The final blend was discharged and the yield recorded.

The blend was tableted on a Cad Mach 16 station tablet press equipped with two stations of 0.625", isometric-coated, flat-faced, standard beveled tools positioned opposite each other, and using a gravity feed system.

The components and physical characteristics of the effervescent tablets thus formed are given in Table 3.

TABLE 3-1

TABLET FORMULATION (mg/tablet)

| Expermnent # | 4A | 4B | 4C | 4D | 4E |
|---|---|---|---|---|---|
| MATERIALS | | | | | |
| Ranitidine HCl Microcaps | 153.72 | 207.76 | 134.0 | 155.83 | 159.44 |
| Dextrose, Anhydrous, Milled | 347.78 | 293.74 | 367.50 | 345.67 | 342.06 |
| Sodium Bicarbonate, USP 1 | 116.0 | 116.0 | 116.0 | 116.0 | 116.0 |
| Citric Acid, Anhyd. USP FG | 72.0 | 72.0 | 72.0 | 72.0 | 72.0 |
| Potassium Carbonate, Milled | 10.0 | 10.0 | 10.0 | 10.0 | 10.0 |
| Aspartame, NF | 38.0 | 38.0 | 38.0 | 38.0 | 38.0 |
| Flavor 17.42.7356 | 5.0 | 5.0 | 5.0 | 5.0 | 5.0 |
| Saccharin Sodium, USP | 1.5 | 1.5 | 1.5 | 1.5 | 1.5 |
| Silicon Dioxide, NF | 1.0 | 1.0 | 1.0 | 1.0 | 1.0 |
| Magnesium Stearate, NF | 5.0 | 5.0 | 5.0 | 5.0 | 5.0 |
| Total | 750.0 | 750.0 | 750.0 | 750.0 | 750.0 |

TABLE 3-2

| PHYSICAL DATA | Tablet Wt. (mg) | 753 | 748 | 753 | 750 | 752 |
|---|---|---|---|---|---|---|
| | % RSD | 1.01 | 0.853 | 0.868 | 10.1 | 1.16 |
| | Thickness (in.) | 0.126 | 0.132 | 0.126 | 0.126 | 0.127 |
| | % RSD | 0.712 | 0.536 | 0.712 | 1.03 | 0.964 |
| | Hardness (n) | 13 | 10 | 13 | 13 | 11 |
| | % RSD | 13.3 | 12.8 | 22.9 | 10.2 | 18.2 |
| | Batch Size (gm) | 562.5 | 562.5 | 562.5 | 562.5 | 562.5 |

EXAMPLE 5

The effervescent tablets prepared in Example 4 were evaluated with respect to drug release over time upon contact with water. Conditions for dissolution testing were as follows.

Media: Water
Media Volume: 900 mL
Media Temperature: 37° C.
Apparatus: USP #2 (Paddles)
Paddles Speed: 50 RPM The rate of dissolution for these tablets is given in Table 4. Reproducibility of tablet dissolution at times ranging from 7.5 to 60 minutes can be seen by comparison of the percent dissolution of the tablets made in Experiments 4A through 4E at any of the time points tested.

TABLE 4

ANALYSIS OF TABLETS

| EXPERIMENT # | 4A | 4B | 4C | 4D | 4E |
|---|---|---|---|---|---|
| Tablet Assay | 72.86 mg/tab | 79.46 mg/tab | 74.23 mg/tab | 72.95 mb/tab | 75.87 mb/tab |
| Tablet Dissolution | | | | | |
| 7.5 min | 93.8% | 90.5% | 96.0% | 93.0% | 93.7% |
| 15 min | 97.1% | 95.3% | 97.7% | 96.0% | 96.9% |
| 22.5 min | 97.6% | 96.4% | 97.8% | 96.7% | 97.5% |
| 30 min | 98.0% | 97.0% | 98.0% | 97.0% | 97.9% |
| 45 min | 98.6% | 97.7% | 98.2% | 97.2% | 98.3% |
| 60 min | 98.9% | 98.0% | 98.5% | 97.7% | 98.5% |

EXAMPLE 5

Taste-Masking

Microcapsules containing ranitidine hydrochloride were prepared as described in Example 2. Effervescent tablets containing the microcapsules were prepared as described in Example 4.

The microcapsules and effervescent tablets were evaluated for taste-masking by an internal taste panel of eight individuals, each of whom evaluated all of the microcapsules. Four of the five tablet formulations were evaluated by the same eight individuals. Taste evaluation was performed using a standard protocol consisting of: eating a soda cracker; taking a sip of water; and tasting the microcapsule or tablet sample. This sequence was repeated by each subject until all of the samples had been evaluated.

Figure 1B:
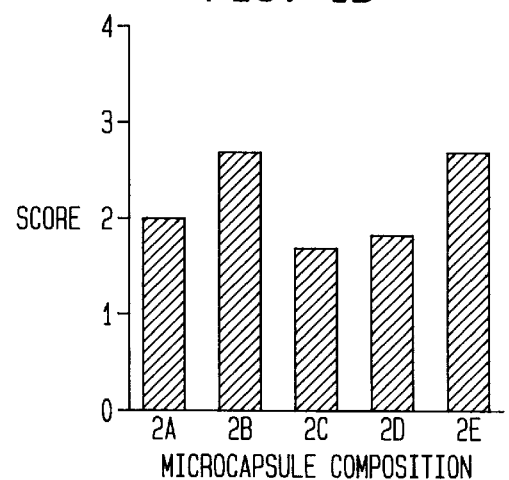
Figure 1C:
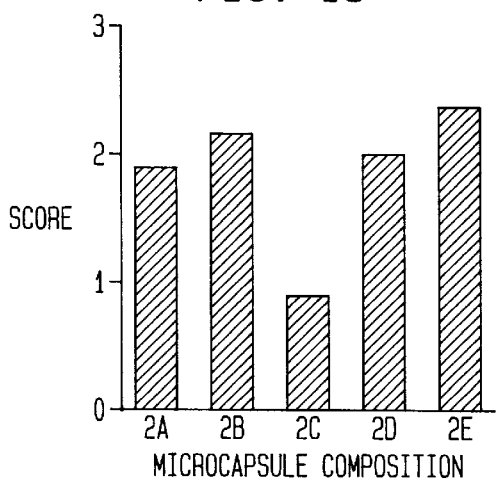
Figure 1D:
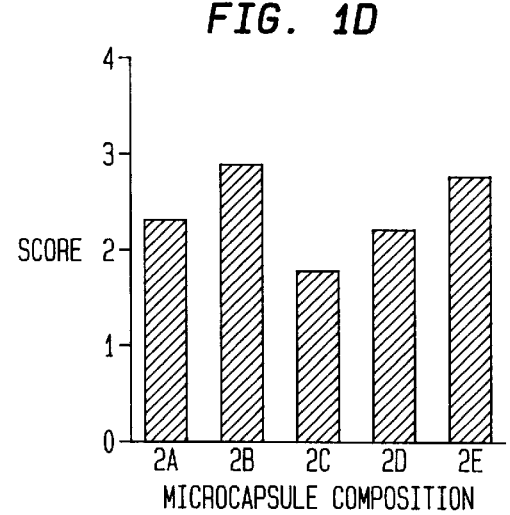
Figure 2A:
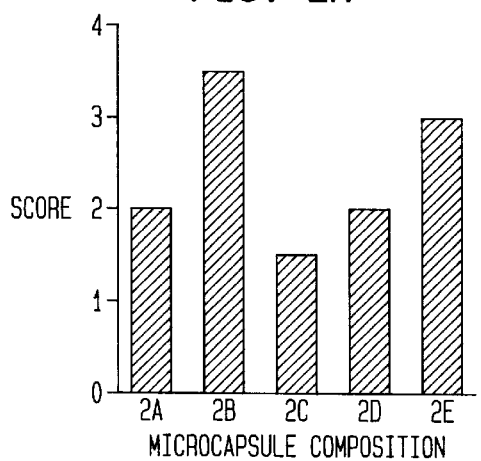
FIG. 2A, FIG. 2B, FIG. 2C, and FIG. 2D depict the median scores for the evaluation described in Example 6 of taste masking, bitterness, aftertaste, and overall acceptance, respectively, of ranitidine microcapsule compositions.
Figure 2B:
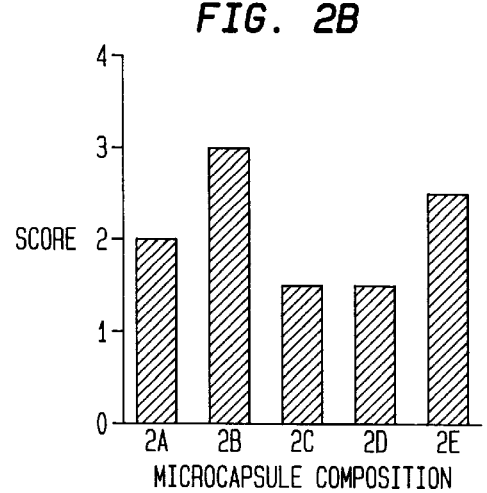
Figure 2C:
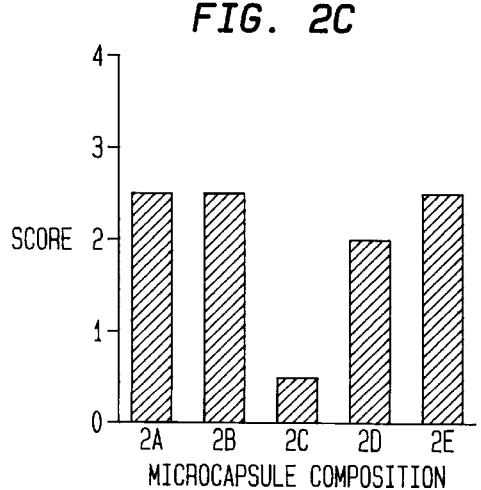
Figure 2D:
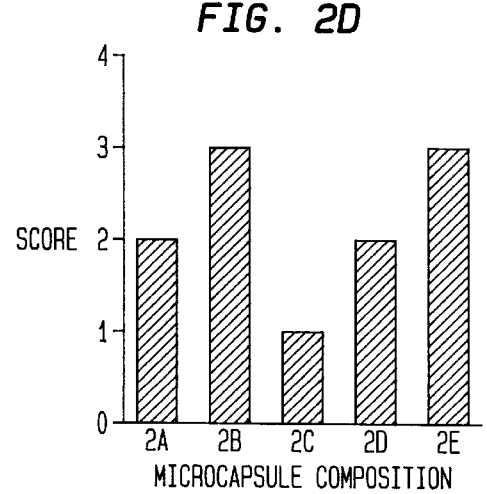

Microcapsules were evaluated for the following characteristics: flow, color, odor, mouthfeel/grittiness, taste masking, bitterness, aftertaste, and overall acceptance. The average and median scores for microcapsule taste masking, bitterness, aftertaste, and overall acceptance are shown in FIG. 1A through FIG. 1D, and FIG. 2A through FIG. 2D, respectively. The data are presented on a scale of 0 to 5, with 5 being the most desirable result, i.e., no bitterness or aftertaste, and 0 being the least desirable score, i.e., no taste masking. Thus, for example, microcapsule composition 2B appears to have the best taste masking score and best overall score.

Figure 3A:
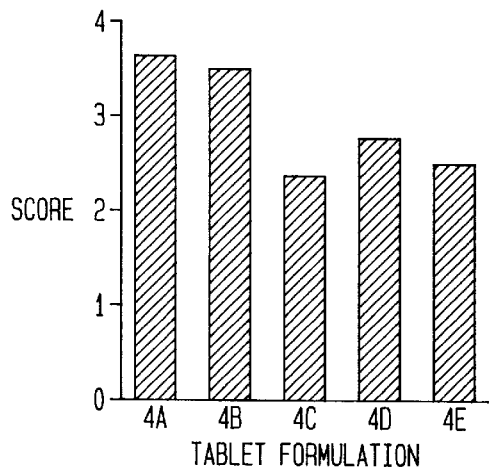
FIG. 3A, FIG. 3B, FIG. 3C, and FIG. 3D depict the average scores for the evaluation described in Example 6 of taste masking, bitterness, aftertaste, and overall acceptance, respectively, of ranitidine tablet formulations.
Figure 3B:
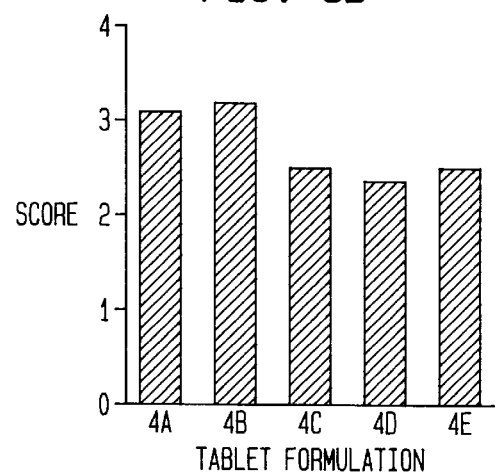
Figure 3C:
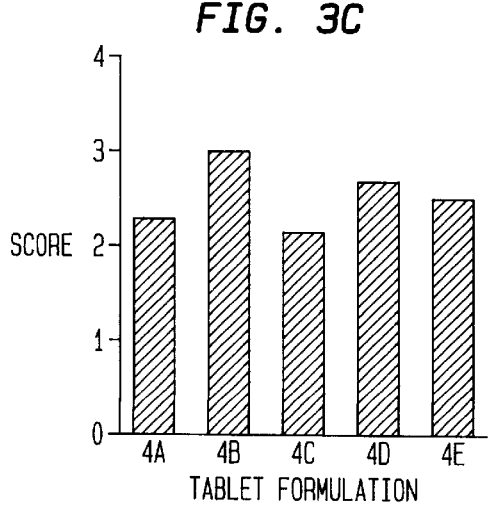
Figure 3D:
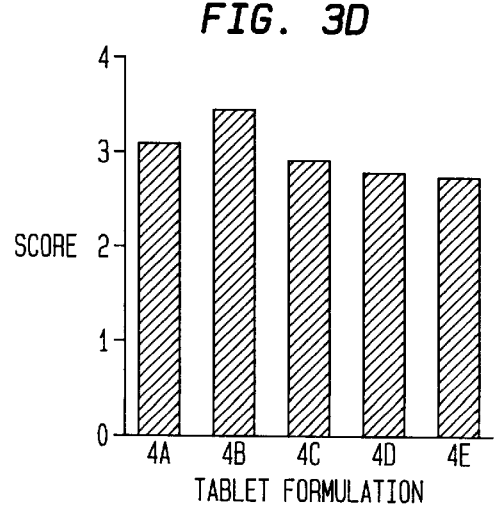
Figure 4A:
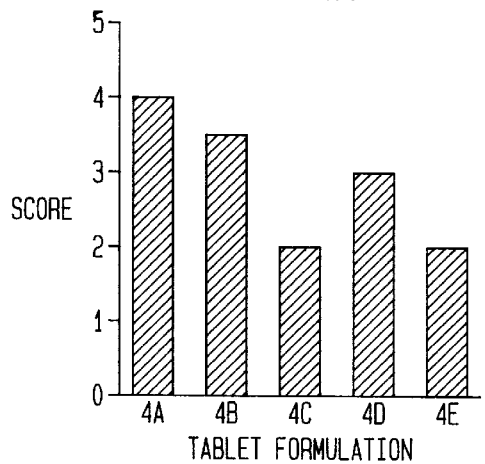
FIG. 4A, FIG. 4B, FIG. 4C, and FIG. 4D depict the median scores for the evaluation described in Example 6 of taste masking, bitterness, aftertaste, and overall acceptance, respectively, of ranitidine tablet formulations.
Figure 4B:
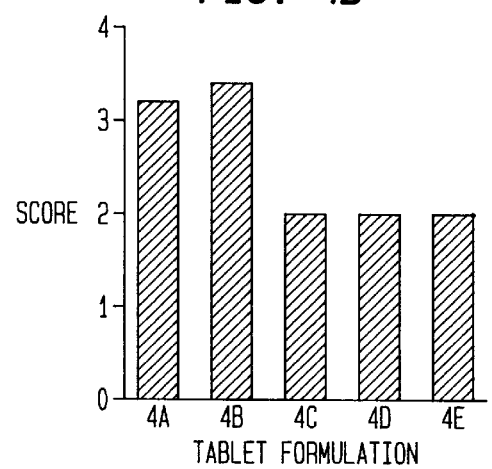
Figure 4C:
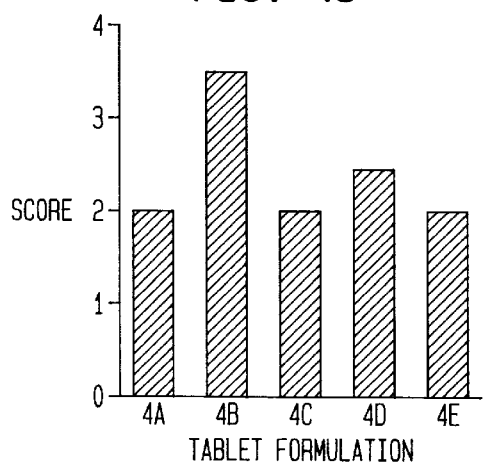
Figure 4D:
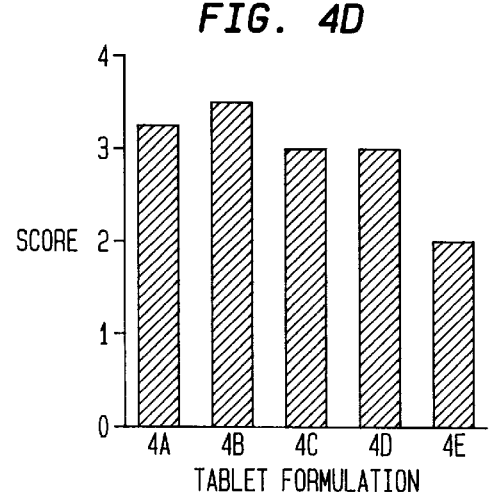

Tablet formulations were evaluated for: disintegration time, effervescence level, flavor acceptance, mouthfeel, taste masking, bitterness, aftertaste, and overall acceptance. The average and median scores for microcapsule taste masking, bitterness, aftertaste, and overall acceptance are shown in FIG. 3A through FIG. 3D, and FIG. 4A through FIG. 4D, respectively. Tablet formulation 4B, prepared from microcapsule composition 2B, appeared to have the best -taste masking score and the best overall score.

What is claimed is:

1. A taste-masked microcapsule composition of a water soluble drug, the composition comprising microcapsules of the water soluble drug in a coacervated polymeric material consisting essentially of one or more polymers selected from the group consisting of ethyl cellulose, cellulose acetate phthalate, cellulose acetate butyrate, polymethacrylates, hydroxypropyl methyl cellulose phthalate; carboxymethyl ethylcellulose; polylactic acid and combinations thereof, said polymeric material constituting approximately 30 wt. % to 65 wt. % of the composition, said microcapsules being effective to provide targeted release of said drug.

2. A taste-masked microcapsule composition of a drug selected from the group consisting of $H_2$ antagonists and pharmaceutically acceptable salts thereof, the composition comprising microcapsules of the drug in a coacervated polymeric material consisting essentially of one or more polymers selected from the group consisting of ethyl cellulose, cellulose acetate phthalate, cellulose acetate butyrate, polymethacrylates, hydroxypropyl methyl cellulose phthalate; carboxymethyl ethylcellulose; polylactic acid and combinations thereof, said polymeric material constituting approximately 30 wt. % to 65 wt. % of the composition, said microcapsules being effective to provide targeted release of said drug.

3. A taste-masked microcapsule composition of a water soluble drug, comprising microcapsules of said drug in a coacervated polymeric material, said polymeric material constituting approximately 30 wt. % to 65 wt. % of the composition, said microcapsules being effective to provide targeted release of said drug.

4. A taste-masked microcapsule composition of a drug selected from the group consisting of $H_2$ antagonists and pharmaceutically acceptable salts thereof, comprising microcapsules of said drug in a coacervated polymeric material, said polymeric material constituting approximately 30 wt. % to 65 wt. % of the composition, said microcapsules being effective to provide targeted release of said drug.

5. The taste-masked microcapsule composition of claim 3 or claim 4, wherein the coacervated polymeric material consists essentially of a substantially water-insoluble polymer.

6. The taste-masked microcapsule composition of claim 5 wherein said coacervated polymeric material has pores therein and said microcapsules are adapted to release the drug by diffusion through said pores.

7. The taste-masked microcapsule composition of claim 6 wherein said coacervated polymeric material consists essentially of one or more polymers substantially impervious to diffusion of the drug through the bulk of the polymer.

8. The taste-masked microcapsule composition of claim 3 or claim 4 wherein said coacervated polymeric material consists essentially of one or more polymers selected from the group consisting of ethyl cellulose, cellulose 25 acetate phthalate, cellulose acetate butyrate, polymethacrylates, hydroxypropyl methyl cellulose phthalate; carboxymethyl ethylcellulose; polylactic acid and combinations thereof.

9. The taste-masked microcapsule composition of claim 1 or claim 2 or claim 3 or claim 4 wherein said coacervated polymeric material is selected from the group consisting of ethyl cellulose, cellulose acetate phthalate, cellulose acetate butyrate, and polymethacrylates.

10. The taste-masked microcapsule composition of claim 9, wherein said coacervated polymeric material is ethyl cellulose.

11. The taste-masked microcapsule composition of claim 1 or claim 2 or claim 3 or claim 4, wherein each microcapsule includes a cores of the drug surrounded by a coating of the coacervated polymeric material.

12. The taste-masked microcapsule composition of claim 1 or claim 2 or claim 3 or claim 4, wherein the water-insoluble polymeric material represents approximately 40 wt. % to 60 wt. % of the formulation.

13. The taste-masked microcapsule composition of claim 1 or claim 2 or claim 3 or claim 4, wherein the water-insoluble polymeric material represents approximately 45 wt. % to 55 wt. % of the formulation.

14. A taste-masked microcapsule composition as claimed in claim 1 or claim 2 or claim 3 or claim 4, wherein said drug is selected from the group consisting of water-soluble $H_2$-antagonists and water soluble pharmaceutically acceptable salts of $H_2$-antagonists.

15. A taste-masked microcapsule composition as claimed in claim 14 wherein said drug is selected from the group consisting of ranitidine and pharmaceutically acceptable salts thereof.

16. The composition of claim 15, wherein the drug is ranitidine hydrochloride.

17. A pharmaceutical formulation for administering a drug, comprising the taste-masked microcapsule composition of claim 1 or claim 2 or claim 3 or claim 4 in the form of a compressed tablet.

18. The pharmaceutical formulation of claim 17, wherein the tablet is chewable.

19. The pharmaceutical formulation of claim 17, wherein the tablet is effervescent.

20. The pharmaceutical formulation of claim 17, wherein the tablet comprises, in addition to the taste-masked microcapsule composition, a dry solid carbonate component and an organic acid, in combination representing on the order of approximately 1 wt. % to 90 wt. % of the tablet.

21. The pharmaceutical formulation of claim 17, wherein the dry solid carbonate component and an organic acid in combination representing on the order of approximately 2 wt. % to 50 wt. % of the tablet.

22. The pharmaceutical formulation of claim 17, wherein the dry solid carbonate component and an organic acid in combination representing on the order of approximately 2 wt. % to 25 wt. % of the tablet.

23. A pharmaceutical formulation for administering a drug, comprising the taste-masked microcapsule composition of claim 1 or claim 2 or claim 3 or claim 4 in the form of a free-flowing particulate material.

24. A pharmaceutical formulation for administering a drug, comprising the taste-masked microcapsule composition of claim 1 or claim 2 or claim 3 or claim 4 in the form of a liquid dispersion.

25. A method for masking the taste of a drug, comprising:
- (a) forming a mixture including (i) the drug; (ii) a first polymeric material effective to microencapsulate the drug, (iii) a second polymeric material for promoting phase separation of the first polymeric material from the solvent, and (iv) a nonpolar organic solvent at a first temperature so that the first and second polymeric materials are dissolved in the solvent;
- (b) cooling the mixture for a time period, at a cooling rate and to a second temperature lower than said first temperature so as to form microcapsules of the drug in the first polymeric material, thereby forming a dispersion of microencapsulated drug;
- (c) removing the solvent and second polymeric material from the 20 dispersion, to provide isolated taste-masked microcapsules; and
- (d) drying the microcapsules;
- wherein the relative amounts of drug and first polymeric material in step (a) are such that the microcapsules contain approximately 30 wt. % to 65 wt. % first polymeric material and said microcapsules are effective to provide targeted release of the drug.

26. The method of claim 25, wherein the first polymeric material is a substantially water-insoluble polymer.

27. The method of claim 25, wherein the first polymeric material is selected from the group consisting of ethyl cellulose, cellulose acetate phthalate, cellulose acetate butyrate, polymethacrylates, hydroxypropyl methyl cellulose phthalate; carboxymethyl ethylcellulose; polylactic acid and combinations thereof.

28. The method of claim 25, wherein the first polymeric material is selected from the group consisting of ethyl cellulose, cellulose acetate phthalate, cellulose acetate butyrate, and polymethacrylates.

29. The method of claim 28, wherein the first polymeric material is ethyl cellulose.

30. The method of claim 25, wherein the first polymeric material represents approximately 40 wt. % to 60 wt. % of the formulation.

31. The method of claim 30, wherein the first polymeric material represents approximately 45 wt. % to 55 wt. % of the formulation.

32. The method of claim 25 wherein said drug is selected from the group consisting of water-soluble $H_2$-antagonists and pharmaceutically acceptable salts thereof.

33. The method of claim 25 wherein said drug is selected from the group consisting of ranitidine and pharmaceutically acceptable salts thereof.

34. The method of claim 25, wherein the drug is ranitidine hydrochloride.

35. The method of claim 25, wherein said step of forming said mixture includes the steps admixing said first and second polymers with said solvent to form a blend, heating said blend to said first temperature and maintaining said blend at said first temperature until said polymers are dissolved in said solvent, then adding said drug.

36. The method of claim 25 wherein said step of forming said mixture includes the steps of admixing said drug and said polymers with said solvent to form a blend, and then heating said blend to said first temperature.

37. A method for masking the taste of a drug, comprising:
- (a) forming a mixture including (i) the drug and (ii) a first polymeric material effective to microencapsulate the drug, and (iii) a nonpolar organic first solvent at a first temperature so that the first and second polymeric materials are dissolved in the solvent;
- (b) cooling the mixture for a time period, at a cooling rate to a second temperature lower than said first temperature so as to form microcapsules of the drug in the first polymeric material, thereby forming a dispersion of microencapsulated drug;
- (c) removing the solvent from the dispersion, to provide isolated taste-masked microcapsules; and
- (d) drying the microcapsules;
- wherein the relative amounts of drug and first polymeric material in step (a) are such that the microcapsules contain approximately 30 wt. % to 65 wt. % first polymeric material and said microcapsules are effective to provide targeted release of the drug.

38. A method as claimed in claim 37 further comprising the step of adding a second solvent effective to promote phase separation of the first polymeric material to said mixture during or prior to said cooling step.

39. The method of claim 37, wherein the first polymeric material is a substantially water-insoluble polymer.

40. The method of claim 37, wherein the first polymeric material is selected from the group consisting of ethyl cellulose, cellulose acetate phthalate, cellulose acetate butyrate, polymethacrylates, hydroxypropxl methyl cellulose phthalate; carboxymethyl ethylcellulose; polylactic acid and combinations thereof.

41. The method of claim 37, wherein the first polymeric material is selected from the group consisting of ethyl cellulose, cellulose acetate phthalate, cellulose acetate butyrate, and polymethacrylates.

42. The method of claim 41, wherein the first polymeric material is ethyl cellulose.

43. The method of claim 37, wherein the first polymeric material represents approximately 40 wt. % to 60 wt. % of the formulation.

44. The method of claim 43, wherein the first polymeric material represents approximately 45 wt. % to 55 wt. % of the formulation.

45. The method of claim 37 wherein said drug is selected from the group consisting of water-soluble $H_2$-antagonists and pharmaceutically acceptable salts thereof.

46. The method of claim 37 wherein said drug is selected from the group consisting of ranitidine and pharmaceutically acceptable salts thereof.

47. The method of claim 37, wherein the drug is ranitidine hydrochloride.

* * * * *